| United States Patent [19] | [11] Patent Number: 4,637,932 |
| Pancham | [45] Date of Patent: Jan. 20, 1987 |

[54] PROCESS FOR PRODUCING A CONCENTRATE ENRICHED IN COAGULATION FACTORS VII AND VIIA

[75] Inventor: Nazreen Pancham, San Francisco, Calif.

[73] Assignee: Miles Laboratories, Inc., Elkhart, Ind.

[21] Appl. No.: 660,762

[22] Filed: Oct. 15, 1984

[51] Int. Cl.⁴ .............................................. A61K 35/16
[52] U.S. Cl. .................................................... 424/101
[58] Field of Search ......................................... 424/101

[56] References Cited

U.S. PATENT DOCUMENTS

| 4,456,591 | 6/1984 | Thomas | 424/101 |
| 4,470,969 | 9/1984 | Pancham | 424/101 |
| 4,473,553 | 9/1984 | Zuffi et al. | 424/101 |
| 4,479,938 | 10/1984 | Thomas | 424/101 |

*Primary Examiner*—Sam Rosen
*Attorney, Agent, or Firm*—Pamela A. Simonton

[57] ABSTRACT

There is disclosed an improved process for producing a concentrate containing coagulation factors VII and VIIa in relatively high purity by contacting an aqueous preparation containing factors VII and VIIa with a divalent metal salt adsorbent having selective affinity for calcium-binding coagulation factors and eluting the coagulation factors therefrom, and contacting the eluate with an anionic exchange resin and selectively eluting coagulation factors VII and VIIa therefrom by step or gradient elution techniques to obtain factors VII and VIIa in high yield, free of other coagulation factors and other proteins. In one embodiment of this invention Cohn Effluent I may be used as the source of factors VII and VIIa.

13 Claims, No Drawings

PROCESS FOR PRODUCING A CONCENTRATE ENRICHED IN COAGULATION FACTORS VII AND VIIA

BACKGROUND OF THE INVENTION

1. Field of the Invention: This invention relates to the blood coagulation components Factors VII and VIIa, and to a process for producing a blood coagulation promoting product containing Factors VII and VIIa in high yield and relative purity and free from other coagulation factors.

2. Cross-reference: The present application is related to U.S. Pat. Nos. 4,470,969 and 4,473,553, both of which are owned with the present application by a common assignee. These related applications concern processes for producing coagulation factors VII and VIIa by contacting aqueous preparations containing the factors VII and VIIa with a lipoprotein binding adsorbent, contacting the resulting lipoprotein-poor solution with an adsorbent having selective affinity for calcium-binding coagulation factors and selectively eluting factors VII and VIIa therefrom. As the lipoprotein binding adsorbent, there is used in U.S. Pat. No. 4,470,969 a polyanionic adsorbent in combination with divalent metal ions whereas there is used in U.S. Pat. No. 4,473,553 polyethylene glycol.

3. Description of the Prior Art and Related Art: U.S. Pat. Nos. 3,717,708, 4,404,132 and 4,361,510 disclose a blood coagulation promoting complex concentrate product free of thrombin, heparin, activated Factor X, depressor activity, and anticomplement activity, and containing coagulation Factors II, VII, IX and X in non-activated form. More particularly, U.S. Pat. No. 3,717,708 discloses the product described above produced by a process comprising the steps of applying Cohn Supernatant I (also referred to as "Cohn Effluent I"), prepared by Method 6 from unmodified citrated human plasma, which contains Factors II, VII, IX and X, onto an anion exchange resin consisting of cross-linked dextran chains with diethyl-aminoethyl groups attached by ether linkages to the glucose units of the polysaccharide chains (e.g. DEAE Sephadex ®, Pharmacia Fine Chemicals, Inc.) and adsorbing thereon the given coagulation Factors; selectively eluting the anion exchange resin from the preceding step with ammonium bicarbonate solution of pH in the range of 7.3 to 8.2 and of increasing molarity between 0.3M and 0.75M; separating the eluate containing the given coagulation Factors; freezing the separated eluate and removing the ammonium bicarbonate therefrom by lyophilizing the frozen fraction. U.S. Pat. Nos. 4,404,132 and 4,361,510, each arising out of a common parent application, now-abandoned, disclose improvements in the above-described process and product of U.S. Pat. No. 3,717,708 wherein the elution step is carried out with an aqueous solution containing a non-volatile salt and citrate ions in place of an aqueous solution of the volatile salt, ammonium bicarbonate, and wherein a combined ultrafiltration-diafiltration step is used in place of lyophilization to remove ammonium bicarbonate, these improvements providing a product having greater Factor IX specific activity than that of the product from U.S. Pat. No. 3,717,708.

Thomas, U.S. Pat. No. 4,287,180 discloses a method for treating a patient having an inhibitor of blood clotting factors by administering to the patient a therapeutically effective dose of an aqueous composition including, in units/ml, factor VIII correctional activity, about 2-35; prothrombin, about 1-10; thrombin, less than 0.003; factor VII, about 37-190; factor VIIa, about 8-80; factor IX, about 15-112; factor IX precursor, 0-30; factor X, about 1-30; and factor Xa, about 1-10.

Thomas, U.S. Pat. No. 4,357,321, a division of U.S. Pat. No. 4,287,180 mentioned above, discloses a method for treating a patient having an inhibitor of blood clotting factor by administering to the patient a therapeutically effective does of an aqueous composition of 37-110 units/ml of factor VII and 8-80 units/ml of factor VIIa.

In both of the foregoing Thomas patents, there is disclosed the use of Cohn plasma fractions I+II+III, I and III, II and III, III, III-0, IV-1, or IV-1 and IV-4. IV-1 is the preferred fraction and is disclosed in the working examples. The starting compositions are dissolved in a buffer or saline to a concentration of about 10% weight/volume at about 20° C., screened for clotting factor activity to determine the degree of preexisting spontaneous activation, partially purified by adsorption onto a suitable, known prothrombin complex adsorbent (e.g. tribasic calcium phosphate or a diethylaminoethyl group substituted resin), followed by elution from the adsorbent in a volume of about 4% of the volume of the dissolved Cohn fraction, none of the volumes or temperatures being critical. Example 1 of the patent illustrates a typical manufacturing run for the preparation of an activated PCC (prothrombin complex) according to the invention of the patent wherein the starting material, a Cohn fraction IV-1 paste, is suspended in saline at a pH of 7.2; a resultant precipitate is allowed to settle; and a clear supernatant is obtained by centrifugation. Then calcium phosphate is added to the supernatant, the calcium phosphate adsorbed coagulation factors are recovered, the factors separated from calcium phosphate by vigorous mixing with a volume of 0.1M sodium citrate equal to 4% of the dissolved paste, and the resulting suspension is centrifuged and the supernatant is recovered. Following this, the coagulation factors in the supernatant are activated by contacting the supernatant with silica and the activated PCC is further purified by PEG precipitation steps followed by dissolution of the precipitate in 0.02M sodium citrate, sterile filtration and lyophilization.

Thomas, U.S. Pat. No. 4,382,083 and PCT publication WO No. 83/00016 which corresponds thereto, disclose a method for treating a patient having a clotting factor defect by administering a composition of an effective hemostatic amount of factor VIIa, which composition is uncontaminated by other activated blood clotting factors having sufficient activity alone to produce a hemostatic effect. Unactivated precursor forms of factors may be present in the compositions and the amounts of unactivated factors II, VII, IX and X typically range from about 1-10, 20-250, 0-30, and 1-30 units/ml, respectively. Preferably, the compositions are essentially free of factors IX and II but contain factors VII and/or X in the above concentrations. Suitable factor VIIa compositions for use according to the patented method can be produced according to the methods of Kisiel et al, *Biochemistry*, 16 (9), 4189 (1977) or Broze and Majerus, *J. Biol. Chem.*, 255, 1242 (1980).

Kisiel et al, supra, disclose a 5-step procedure to isolate and purify factor VII from bovine plasma which involves barium sulfate adsorption and elution, DEAE Sephadex ® batchwise adsorption and elution, benzamidine-agarose column chromatography, heparin-agarose column chromatography, and preparative polyacrylamide gel disc electrophoresis.

Broze and Majerus, supra, disclose the purification of human factor VII from human, citrated, fresh frozen plasma with platelets removed by barium citrate adsorption and elution and ammonium sulfate fractionation. The resulting solution was then treated to two successive QAE-Sephadex chromatographic purification steps followed by gel filtration on Sephadex G-100.

Bajaj et al, *J. Biol. Chem.*, 356 (1), 253 (1981), disclose the purification of human factor VII from blood plasma using barium citrate adsorption, ammonium sulfate fractionation, DEAE-Sephadex chromatography, preparative polyacrylamide gel electrophoresis (PAGE), and SDS-PAGE.

Gladhaug et al, *Biochim. Biophys. Acta,* 215, 105 (1970), disclose the purification of factors VII and X from human serum using barium sulfate-Sephadex, DEAE-Sephadex, polyacrylamide gel filtration, and polyacrylamide gel disc electrophoresis.

Current thinking in the field to which this invention pertains is that there are two separate systems—intrinsic and extrinsic—which can promote clotting and can thereby participate in normal hemostasis. In factor VIII deficient persons, who also have circulating antibodies to the molecule, replacement therapy with factor VIII concentrates has been shown to be of limited or of no value, presumably because the intrinsic system in such persons has been largely inhibited. Treatment with prothrombin complex products, however, has had varying degrees of success in these patients; but the active principal in these materials has not, as yet been elucidated. It is not unlikely that these products function by simply enhancing the contribution of the extrinsic system to clotting, taking into consideration that they contain concentrated amounts of some of the extrinsic system enzymes, namely, factors II, VII and X, more specifically, these products may function as follows: Factor VII/VIIa levels are raised to the extent that appreciable levels of tissue factor VII/VIIa complex are formed. This complex can interact with both of factors IX and X and, if this occurs, a series of activations can arise. Activated factor X is known to be able to activate factor VII and factor IX reciprocally, to be autoactivatable, and to activate factor II. The net effect of any of these reactions would thus be a great increase of factor Xa and, hence, factor IIa activity, which would further result in subsequent clot formation.

Crucial to the above-described scheme is the concept that the activation remains localized to prevent systemic, uncontrolled clot formation. Under normal conditions, this danger is avoided probably because tissue factor may be fairly selectively exposed at the site of injury keeping the activations within a local environment and also because of the presence of circulating, naturally occurring protease inhibitors.

That activation can occur at all in the presence of these circulating inhibitors, even in a local environment, may be due to the reciprocal activations of factors VII, IX and X. Although it is generally accepted that the extrinsic system can function as described at least in vitro, it is not understood why the extrinsic system does not control bleeding in factor VIII deficient persons. It is conceivable that the extrinsic system under normal circumstances acts only as an auxiliary to the intrinsic system to promote clotting. While it may be that the levels of extrinsic system participants are high enough to repair certain kinds, or limited amounts of, physiologic damage, they may not be sufficient to correct the major bleeding episodes that occur in factor VIII or IX deficiencies. According to the above, factor VII would be a requirement in order for the described reciprocal activations to occur.

There is a need, then, for a process to produce factor VII and factor VIIa in relatively pure form, free of the other factors, II, IX and X, with which factors VII and VIIa are generally associated and isolated, for both experimental and therapeutic purposes.

SUMMARY OF THE INVENTION

This invention is an improved process for producing a concentrate containing factors VII and VIIa in high yield and relative purity, free of factors II, IX and IXa, and X and Xa, wherein the improvement is the use, as the starting material containing factors VII and VIIa, of a wash solution obtained and then discarded in the process for producing blood coagulation complexes containing factors II, VII, IX and X in non-activated form as disclosed in U.S. Pat. Nos. 3,717,708, and 4,404,132 and 4,361,510, described above. Very generally, these patents disclose processes for producing blood coagulation complexes containing factors II, VII, IX and X by applying a starting material to an anion exchanger to adsorb the desired coagulation factors, washing the exchanger with an aqueous solution containing a volatile salt in the case of U.S. Pat. No. 3,717,708 or a non-volatile salt in the case of U.S. Pat. Nos. 4,361,510 and 4,404,132 wherein the wash solution has an ionic strength sufficient to remove less strongly bound plasma proteins from the anion exchanger but insufficient to remove the adsorbed coagulation factors, and then selectively eluting from the anion exchanger using an aqueous solution containing a volatile salt or non-volatile salt as described above, respectively, except that the aqueous solution has an ionic strength sufficient to elute the adsorbed coagulation factors. Thus, this invention has as its basis the discovery that the heretofore discarded wash solution provides a source material from which there may be obtained high yields of factors VII and VIIa. In another aspect, this invention is a pharmaceutical preparation consisting essentially of the concentrate containing factors VII and VIIa produced according to the process of the invention.

DETAILED DESCRIPTION OF THE INVENTION

This invention is an improved process for producing a concentrate consisting essentially of blood coagulation factors VII and VIIa and having a specific activity in the range of about 500 to 3000 u/$A_{280}$ consisting essentially of the steps of:

(a) providing an aqueous solution of plasma proteins containing factors VII and VIIa;

(b) contacting the aqueous solution from step (a), adjusted to a pH of about 6 to 8, with an adsorbent having selective affinity for calcium-binding proteins, including factor VII, selected from the group of water-insoluble divalent metal salts, to adsorb the calcium-binding proteins;

(c) selectively eluting, by techniques selected from step and gradient elution techniques, factors VII and VIIa, from the protein-bound adsorbent from step (b) by the addition of a buffer solution containing suitable soluble salts effective to displace the bound proteins and collecting the eluate pool;

(d) contacting the eluate pool from step (c), adjusted to a pH of about 3 to 11, with an anionic exchange resin having affinity for the calcium-binding proteins, including factors VII and VIIa, and adsorbing thereon the calcium-binding proteins; and (e) selectively eluting, by techniques selected from step and gradient elution techniques, factors VII and VIIa from the protein-bound adsorbent from step (d) by the addition of a buffer solution containing suitable salts in increasing ionic strength; wherein the improvement comprises using as the starting aqueous solution containing coagulation factors VII and VIIa in step (a) an aqueous wash eluate, containing about 0.1–0.45M of at least one of ammonium bicarbonate, sodium bicarbonate and sodium chloride and containing 0.05–0.2M of citrate ions, obtained by contacting a plasma fraction containing coagulation factors II, VII, IX and X with an anion exchange resin and washing the anion exchange resin having adsorbed thereto plasma proteins contained in said plasma fraction to remove those plasma proteins that are less strongly bound to the anion exchange resin so as to be removeable by contacting the anion exchange resin having adsorbed thereto said plasma proteins with a wash solution containing 0.1–0.45M of at least one of ammonium bicarbonate, sodium bicarbonate and sodium chloride.

In a preferred embodiment, the starting aqueous solution containing coagulation factors VII and VIIa may be obtained by first contacting Effluent I (also referred to as Cohn Supernatant I, prepared by Cohn Method 6 as disclosed in U.S. Pat. No. 2,390,074 and *J. Amer. Chem. Soc.*, 68, 459 [1946]) with an anion exchange resin, for example DEAE (diethylaminoethyl) Sephadex® consisting of cross-linked dextran chains with diethylaminoethyl groups attached by either linkages to the glucose units of the polysaccharide chains, supplied by Pharmacia Fine Chemicals, Inc. Then, the anion exchanger is washed to remove those plasma proteins that are less strongly bound to the anion exchanger than are the coagulation factors II, IX and X using a non-volatile salt, e.g. sodium chloride or carbonate, solution having an ionic strength, that is, a concentration of sodium chloride of about 0.1–0.3M and containing citrate ions (e.g. sodium citrate or the like) in a concentration of about 0.05–0.2M. When there is used a non-volatile salt such as sodium chloride in the wash solution, it is more preferred to use a wash solution 0.2M in sodium chloride and 0.1M in sodium citrate.

In a more preferred embodiment, the starting aqueous solution containing coagulation factors VII and VIIa may be obtained as described above except that the anion exchanger is washed using a volatile salt, e.g. ammonium bicarbonate solution having a concentration of 0.2–0.3M, most preferably 0.3M.

The adsorbent having selective affinity for calcium-binding proteins used in step (b) preferably is selected from any member of the water-insoluble divalent metal salts, preferably those salts wherein the divalent metal is calcium, magnesium or barium and wherein the anion is phosphate, sulfate or citrate. Other adsorbents which may be used in place of the water-insoluble divalent metal salt include polysaccharide adsorbents such as those which are used in step (d). Step (b) may be conveniently carried out using column or batch chromatographic techniques. Most preferably, the water-insoluble divalent metal salt is tricalcium phosphate, whose common name is hydroxyapatite. The process of the invention can be conveniently carried out using, in step (b), a preferred pH of 5 to 8.

As an example of a suitable buffer in step (c), there may be mentioned MES and TRIS buffers and as a suitable salt there may be mentioned sodium phosphate.

The anionic exchange resin adsorbent used in step (d) is preferably a polysaccharide adsorbent selected from the group of polygalactose, polydextran and cellulose resins wherein the polysaccharide chains have positively charged groups, e.g. diethylaminoethyl groups or quaternary ethyl amino groups, attached to the glucose units in the polysaccharide. Examples of suitable polysaccharide adsorbents, as the anionic exchange resin, include commercially available anionic exchange resins such as DEAE-Sepharose, DEAE-Sephadex and DEAE-cellulose. Most preferably, the anionic exchange resin is DEAE-Sepharose. Step (d) may be conveniently carried out using column or batch chromatographic techniques wherein the adsorbent, for example, DEAE-Sepharose, is equilibrated in MES-saline. It is known in the art that the conditions of ion exchange in step (e) is temperature dependent. The temperature is not critical and can be in the range of about 4° C.–25° C. For example, at room temperature (about 25° C.), the ionic strength of the salt may be in the range of 0.1–0.4M. As an example of a suitable salt useful in the selective elution step there may be mentioned sodium chloride. A preferred pH for step (d) is 5 to 8 for convenience.

To provide the starting aqueous plasma protein solution, in addition to the preferred Effluent I there may be used any material or plasma fraction or plasma containing factors VII and VIIa, including media taken from the culture of cells, microorganisms, and the like.

The particular advantage of the process of this invention is that higher yields of purified Factors VII and VIIa are obtainable by the process according to this invention than are obtainable by prior art processes and the processes of copending applications U.S. Ser. Nos. 577,578 now U.S. Pat. No. 4,473,553 and 557,579 now U.S. Pat. No. 4,470,969. Although the pnenomenon is not clearly understood, the presence of activated factor in the starting material and in intermediate materials appears to be associated with lower yields of purified Factors VII and VIIa. Factors VII and VIIa have been known, generally, to be isolatable along with Factor IX and complexes containing factors II, VII, IX and X and activated forms thereof. And, activated forms of factors II, VII, IX and X appear to generate throughout the preparation of factor IX concentrate products and complexes containing factors II, VII, IX and X. The starting material used in the process for producing the concentrate containing purified factors VII and VIIa according to the present invention appears to have the advantage associated therewith of a much lesser degree or extent of activation than is associated with starting materials which have been used heretofore so that the resulting product is enriched in factor VII in the activated form. This starting material possesses a fuller capacity to provide a high yield of factor VIIa than does starting materials heretofore known.

This invention permits more facile removal and separation of substances which are undesired and which constitute contaminants in the product concentrate containing factors VII and VIIa.

Another of the advantages as will be recognized by those skilled in the art is that the invention permits the recovery of other coagulation factors, including factors II, IX and X and activated forms thereof, free of factors VII and VIIa by further gradient elution in step (e) using a buffer solution containing higher and increasing ionic strength.

The eluate containing factors VII and VIIa obtained in step (e) may then be processed to put it in condition for use. Generally, the eluate is concentrated to reduce its water content by conventional means, for example, by ultrafiltration. Also, the residual salt content in the eluate may be reduced by conventional means, for example, dialysis, diafiltration and the like. The resulting concentrate containing factors VII and VIIa is suitable for use as a pharmaceutical preparation for therapeutic purposes and for experimental purposes. The pharmaceutical preparations may contain any of the conventional pharmaceutical adjuvants and excipients. The pharmaceutical preparations intended for therapeutic use should contain a therapeutically effective amount of factors VII and VIIa, that is, that amount necessary for preventative or curative purposes.

The pharmaceutical preparations comprising the product produced by the process of the invention may be treated using conventional procedures to reduce and eliminate infectious microorganisms and to render the preparations non-viral, particularly non-hepatitis, infective. The pharmaceutical preparations may be sterile-filtered, heat treated, chemically treated, subjected to ultraviolet radiation or treated on colloidal silica. For example, the preparations, in wet or dry state (that is, as the concentrate itself or freeze-dried), may be heated at temperatures of about 60° to 85° C. for a period of several minutes to several days as may be required, generally in the presence of a heat stabilizing agent. Suitable stabilizing agents include nonpolar anions with molecular weights greater than 80, sugars, reduced sugars, and amino acids. Examples of suitable nonpolar anions include salts of carboxylates, hydroxycarboxylates and amino acids such as a sodium or potassium caprylate, caprate, oleate, laurate, valerate, acetylphenylalaninate, acetyleucinate, and acetyltryptophanate. Examples of suitable sugars include glucose, sucrose and maltose to name but a few, and examples of suitable reduced sugars include erythritol and mannitol. Examples of suitable amino acids include lysine, glysine, proline and glutamic acid to name but a few. By way of example without limitation, suitable conventional known processes to reduce or eliminate infectious microorganisms and render the preparations non-viral infective include those disclosed in U.S. Pat. Nos. 3,041,242, 3,057,781, 3,227,626, 4,061,735, 4,137,307, 4,297,344, 2,705,230, 2,897,123, 3,284,301, 3,454,929, 4,379,085 and 4,370,264, 4,440,679, 4,456,590, 4,446,134, and European Patent Publication No. 0058993, and in references disclosed in the patents.

The following examples illustrate but a few embodiments of the present invention and are not to be construed as limiting in scope. All parts and percentages are by weight and temperatures in degrees Celsius unless otherwise indicated.

Characterization of Factor VII/VIIa

Factor VII clotting activity is assayed by the Owren one-stage method using the specific factor-deficient plasma and rabbit-brain thromboplastin containing calcium.

See Owren, P. A. (1949). A quantitative one-stage method for the assay of prothrombin. Scand. J. Clin and Lab. Investigation, 1, 81.

The degree of activation of factor VII is determined by comparing the total clotting activity of f. VII/VIIa with the amidolytic activity of f. VII (the amidolytic activity is insensitive to the state of activation of f. VII) and taking a ratio $$\frac{f.\ VIIc}{f.\ VII_{am}}$$

The amidolytic assay is performed according to the published procedure of Seligsohn et al, *Blood*, Vol. 52, No. 5 (November), 1978.

Factor VII, when activated, is thought to increase clot formation by approximately 50 fold over the native f. VII.

EXAMPLE 1

Step (a)

Effluent I, prepared by the Cohn Method 6, was adsorbed onto DEAE Sephadex according to the procedure described in U.S. Pat. No. 3,717,708 using 10 g (wet weight) of DEAE Sephadex per liter of Effluent I, at about 0°–3° C. The DEAE Sephadex column was washed with 0.2M ammonium bicaro bonate at pH 7–7.8 until not further protein was eluted and the wash was discarded. Then the DEAE Sephadex column was washed with 0.3M ammonium bicarbonate at pH 7–7.8 until no further protein was eluted. The pooled 0.3M ammonium bicarbonate wash solution was concentrated about 20-fold to remove excess salts. Then, the concentrated wash solution was diluted about 20-fold into 0.5M Tris buffer containing 0.15 sodium chloride at about pH 7.5.

Steps (b) and (c)

The diluted 0.3M ammonium bicarbonate wash from step (a) was adsorbed onto tri-calcium phosphate (Hydroxylapatite ®-Bio-Rad) (either in a column mode or batchwise) which was equilibrated with 0.05M Tris, 0.15M NaCl, pH 7.5 buffer. This step was done at room temperature for convenience, but can be done at 4° C. The ratio of swollen resin to sample volume was about 5%. At this ratio virtually all of the factor VII activity is adsorbed. The resin is then washed with equilibrating buffer (several bed volumes) followed by equilibrating buffer containing 1M NaCl. F. VII/VIIa activity was eluted with a phosphate gradient in the case of column chromatography. The mixing chamber contained equilibrating buffer, no phosphate; reservoir contained equilibrating buffer plus 0.35M sodium phosphate. Factor VII/VIIa activity eluted between 0.15 and 0.3M phosphate concentration. Fractions containing peak factor VII/VIIa clotting activity were pooled, concentrated and buffer was exchanged for the next step.

In the case of batch adsorption, stepwise elution of factor VII/VIIa was obtained with equilibrating buffer washes containing increasing amounts of sodium phosphate.

Steps (d) and (e)

The pool containing factor VII/VIIa activity was adsorbed onto DEAE-Sepharose (in a column) equilibrated with 0.02 MES buffer, pH 6.0. Factor VII/VIIa was eluted with a gradient consisting of equilibrating buffer containing 0.1M NaCl in the mixing beaker and equilibrating buffer containing 0.4M NaCl in the reservoir. Factor VII activity eluted between 0.15M and 0.35M NaCl.

The factor VII/VIIa thus prepared was essentially free of other clotting activity, e.g., factor II, IX, X. Trace amounts of activated forms of these clotting factors were evident if insufficient amounts of proteolyte inhibitors were employed during purification.

The results are summarized in the accompanying Table I. The results set forth in Table I below illustrate the advantage achieved by the present invention wherein the process according to the present invention affords a recovery of Factor VIIc of 850%. This recovery represents about a 23-fold improvement over the recovery obtained according to the process of copending U.S. Pat. No. 4,473,553.

TABLE I

Purification and Recovery of Factor VII Clotting Activity (PTC-enriched DEAE)

| Process Step | (F. VIIc) Total F. VII Clotting Units* | (F. VIIAm) Total F. VII Amidolytic Units | % Recovery F. VIIc | Specific Activity | Degree of Activation F. VIIc/F. VIIAm |
|---|---|---|---|---|---|
| 0.3 M $(NH_4)HCO_3$ wash - concentrated | 45,000 | 42,000 | 100% | $\frac{45,000\ u}{136,000\ \text{total units}\ (A_{280})} = 0.33$ | $\frac{45,000}{42,000} = 1.1$ |
| Post Hydroxyapatite (Column Chromatography) | 784,000 | 23,400 | 1750% | $\frac{784,000\ u}{1,502\ \text{total units}\ (A_{280})} = 533$ | 33.5 |
| Post DEAE (Column Chromatography) | 547,000 | N/A | 1215% | $\frac{547,000}{186\ \text{total units}\ (A_{280})} = 2,940$ | N/A |
| Post DEAE concentrated | 383,000 | 7,700 | 850% | $\frac{383,000\ u}{141\ \text{total units}\ (A_{280})} = 2,716$ | $\frac{383,000}{7,700} = 49.7$ |

*F. VII clotting activity derived after incubation of samples with antithrombin-III plus heparin to prevent interaction from other proteases in the estimate of F. VII clotting activity.
N/A Not Applicable

What is claimed is:

1. An improved process for producing a concentrate consisting essentially of blood coagulation factors VII and VIIa and having a specific activity in the range of about 500 to 3000 $u/A_{280}$ consisting essentially of the steps of:
    (a) providing an aqueous solution of plasma proteins containing factors VII and VIIa;
    (b) contacting the aqueous solution from step (a), adjusted to a pH of about 6 to 8, with an adsorbent having selective affinity for calcium-binding proteins, including factor VII, selected from the group of water-insoluble divalent metal salts, to adsorb calcium-binding proteins;
    (c) selectively eluting, by techniques selected from step and gradient elution techniques, factors VII and VIIa from the protein-bound adsorbent from step (b) by the addition of a buffer solution containing suitable soluble salts effective to displace the bound proteins and collecting the eluate pool;
    (d) contacting the eluate pool from step (c), adjusted to a pH of about 3 to 11, with an anionic exchange resin having affinity for the calcium-binding proteins, including factors VII and VIIa, and adsorbing thereon the calcium-binding proteins; and
    (e) selectively eluting, by techniques selected from step and gradient elution techniques, factors VII and VIIa from the protein-bound adsorbent from step (d) by the addition of a buffer solution containing suitable salts in increasing ionic strength;
    wherein the improvement comprises using as the starting aqueous solution containing coagulation factors VII and VIIa in step (a) an aqueous wash eluate, containing about 0.1–0.45M of at least one of ammonium bicarbonate, sodium bicarbonate and sodium chloride and containing 0.05–0.2M of citrate ions, said aqueous solution obtained by (i) contacting a Cohn Effluent I plasma fraction containing coagulation factors II, VII, IX and X with an anion exchange resin and (ii) washing the anion exchange resin having adsorbed thereto plasma proteins contained in said plasma fraction to remove those plasma proteins that are less strongly bound to the anion exchange resin so as to be removeable by contacting the anion exchange resin having adsorbed thereto said plasma proteins with a wash solution containing 0.1–0.45M of at least one of ammonium bicarbonate, sodium bicarbonate and sodium chloride.

2. A process according to claim 1 wherein the starting aqueous solution consists essentially of the wash solution obtained by washing an anion exchange resin column which has been contacted with Cohn Effluent I with an aqueous solution containing 0.1–0.3M sodium chloride and 0.05–0.2M citrate ions.

3. A process according to claim 1 wherein the starting aqueous solution consists essentially of the wash solution obtained by washing an anion-exchange resin column which has been contacted with Cohn Effluent I with an aqueous solution containing 0.2–0.3M ammonium bicarbonate and 0.05–0.2M citrate ions.

4. A process according to claim 2 wherein the anionic exchange resin used consists essentially of cross-linked dextran chains with diethylaminoethyl groups attached by ether linkages to the glucose units of the polysaccharide (dextran) chains.

5. A process according to claim 3 wherein the anionic exchange resin used consists essentially of cross-linked dextran chains with diethylaminoethyl groups attached by ether linkages to the glucose units of the polysaccharide (dextran) chains.

6. A process according to claim 1 wherein the anionic exchange resin used in step (b) is tricalcium phosphate (hydroxyapatite) and the anion exchange resin used in step (d) is a polysaccharide adsorbent selected from the group of polygalactose, polydextran and cellulose resins wherein the polysaccharide chains have positively charged groups selected from diethylaminoethyl groups and quarternary ethyl amino groups attached by to the glucose units in the polysaccharide.

7. A process according to claim 1 wherein the volume of the eluate from step (e) is reduced by ultra-filtration.

8. A process according to claim 1 including the further step of treatment to render the eluate from step (e) non-viral infective and to reduce or eliminate infectious microorganisms.

9. A process according to claim 7 including the further step of treatment to render the eluate from step (e) non-viral infective and to reduce or eliminate infectious microorganisms.

10. A pharmaceutical preparation comprising a product produced according to claim 1.

11. A pharmaceutical preparation comprising a product produced according to claim 7.

12. A pharmaceutical preparation comprising a product produced according to claim 8.

13. A pharmaceutical preparation comprising a product produced according to claim 9.

* * * * *